United States Patent
Kai et al.

(10) Patent No.: US 10,139,401 B2
(45) Date of Patent: Nov. 27, 2018

(54) METHOD FOR CAPTURING TARGET SUBSTANCE, SOLID-PHASE CARRIER FOR CAPTURING TARGET SUBSTANCE, AND METHOD FOR PRODUCING SOLID-PHASE CARRIER

(71) Applicants: JSR CORPORATION, Minato-ku (JP); JSR Life Sciences Corporation, Minato-ku (JP)

(72) Inventors: Hirokazu Kai, Minato-ku (JP); Eiji Takamoto, Minato-ku (JP); Kouji Tamori, Minato-ku (JP)

(73) Assignees: JSR CORPORATION, Minato-ku (JP); JSR Life Sciences Corporation, Minato-ku (JP)

( * ) Notice: Subject to any disclaimer, the term of this patent is extended or adjusted under 35 U.S.C. 154(b) by 0 days.

(21) Appl. No.: 15/117,407

(22) PCT Filed: Feb. 10, 2015

(86) PCT No.: PCT/JP2015/053638
§ 371 (c)(1),
(2) Date: Oct. 24, 2016

(87) PCT Pub. No.: WO2015/119288
PCT Pub. Date: Aug. 13, 2015

(65) Prior Publication Data
US 2017/0138936 A1    May 18, 2017

(30) Foreign Application Priority Data
Feb. 10, 2014 (JP) ................. 2014-022942

(51) Int. Cl.
*G01N 33/543* (2006.01)
(52) U.S. Cl.
CPC . *G01N 33/54306* (2013.01); *G01N 33/54326* (2013.01); *G01N 33/54353* (2013.01); *G01N 33/54393* (2013.01)
(58) Field of Classification Search
None
See application file for complete search history.

(56) References Cited

U.S. PATENT DOCUMENTS

| | | | |
|---|---|---|---|
| 5,986,072 A | 11/1999 | Handa et al. | |
| 6,545,132 B1 | 4/2003 | Handa et al. | |
| 6,767,635 B1 | 7/2004 | Bahr et al. | |
| 2002/0040275 A1* | 4/2002 | Cravatt | C12Q 1/26 702/19 |
| 2002/0160472 A1 | 10/2002 | Handa et al. | |
| 2002/0169293 A1 | 11/2002 | Handa et al. | |
| 2007/0167594 A1 | 7/2007 | Tanaka et al. | |
| 2009/0014682 A1 | 1/2009 | Takahashi et al. | |
| 2010/0196492 A1* | 8/2010 | Green | A61K 9/5146 514/1.1 |
| 2011/0021756 A1 | 1/2011 | Maeno | |
| 2011/0136262 A1* | 6/2011 | Ragavan | G01N 29/022 436/518 |
| 2011/0184155 A1 | 7/2011 | Takahashi et al. | |
| 2013/0149538 A1 | 6/2013 | Takahashi et al. | |
| 2013/0164761 A1 | 6/2013 | Takahashi et al. | |
| 2014/0113977 A1* | 4/2014 | Badea | A61K 47/40 514/778 |

FOREIGN PATENT DOCUMENTS

| | | |
|---|---|---|
| JP | 2000-351814 A | 12/2000 |
| JP | 2003-509034 A | 3/2003 |
| JP | 2007-85929 A | 4/2007 |
| JP | 2013-11479 A | 1/2013 |
| WO | 90/15666 A1 | 12/1990 |
| WO | 2005/037881 A1 | 4/2005 |
| WO | 2006/123686 A1 | 11/2006 |
| WO | 2009/116309 A1 | 9/2009 |
| WO | WO 2012159197 A1 * | 11/2012 ............. A61K 47/40 |

OTHER PUBLICATIONS

International Search Report dated May 19, 2015 in PCT/JP15/053638 Filed Feb. 10, 2015.

* cited by examiner

*Primary Examiner* — Krishnan S Menon
*Assistant Examiner* — Bradley R Spies
(74) *Attorney, Agent, or Firm* — Oblon, McClelland, Maier & Neustadt, L.L.P.

(57) ABSTRACT

To provide a solid-phase carrier that has extremely low nonspecific adsorption of biological substances such as proteins, peptides, nucleic acids and cells, and is capable of maintaining the activity of bound ligands at a high level; and a method for capturing a target substance using the solid-phase carrier.
A method for capturing a target substance, including: a step for preparing a solid-phase carrier for capturing a target substance, the carrier having a base material, at least a portion of the surface thereof being formed of or coated with a saccharide, and having a linker of 5-100 atoms having a reactive functional group for binding a ligand that specifically binds to the target substance, wherein the saccharide is chemically bound to the linker; a step for binding the ligand to the solid-phase carrier to obtain a solid-phase carrier having a ligand bound thereto; and a step for bringing the solid-phase carrier having the ligand bound thereto into contact with a sample containing the target substance that specifically binds to the ligand.

16 Claims, 2 Drawing Sheets

METHOD FOR CAPTURING TARGET SUBSTANCE, SOLID-PHASE CARRIER FOR CAPTURING TARGET SUBSTANCE, AND METHOD FOR PRODUCING SOLID-PHASE CARRIER

TECHNICAL FIELD

The present invention relates to a method for capturing a target substance, a solid-phase carrier for capturing a target substance, and a method for producing the solid-phase carrier.

BACKGROUND ART

In recent years, an attempt to capture a molecule that exhibits a specific interaction with a particular molecule using a technique based on intermolecular interactions, and a research to investigate intermolecular interactions in detail, have been actively conducted. This is specifically represented by the research in which one molecule of the combination of low molecule-low molecule, low molecule-high molecule, or high molecule-high molecule is immobilized onto a solid-phase carrier and the interaction between the two molecules is measured, or the research in which a desired target (a molecule that exhibits a specific interaction with a molecule immobilized onto a solid-phase carrier) is purified on the basis thereof. As examples of various techniques based on intermolecular interactions, a method using an affinity resin is well known.

The presence of a nonspecific intermolecular interaction that prevents the selection and purification of a desired molecule based on a specific intermolecular interaction has raised a problem in that when capturing a target with use of an affinity resin, a nonspecific protein that masks a specific protein during analysis of a protein bound to an affinity resin using, for example, an SDS gel electrophoresis exists, thereby to make the detection of the specific protein difficult.

Patent Literatures 1 to 3 disclose affinity resins. Patent Literature 1 discloses a styrene/glycidyl methacrylate polymer whose surface is covered with glycidyl methacrylate and which binds to a substance via a spacer. Patent Literature 2 discloses magnetic particles for specific trapping comprising: magnetic particles having a particle size of 0.1 to 20 μm and a saccharide, the magnetic particles and the saccharide being chemically bonded, and a probe for specifically trapping a target substance being bonded to the saccharide. Further, Patent Literature 3 discloses a resin obtained by polymerization of a raw material monomer having a hydrophilic spacer incorporated therein.

CITATION LIST

Patent Literature

Patent Literature 1: JP 2000-351814 A
Patent Literature 2: JP 2007-85929 A
Patent Literature 3: WO 2005/037881 W

SUMMARY OF INVENTION

Technical Problem

The problems to be solved by the invention is to provide a solid-phase carrier that has extremely low nonspecific adsorption of biological substances such as proteins, peptides, nucleic acids and cells, and is capable of maintaining the activity of bound ligands at a high level; and a method for capturing a target substance using the solid-phase carrier.

Solution to Problem

The above problem has been solved by the following means.

<1> A method for capturing a target substance, including: a step for preparing a solid-phase carrier for capturing a target substance, the carrier having a base material, at least a portion of the surface thereof being formed of or coated with a saccharide, and having a linker of 5-100 atoms having a reactive functional group for binding a ligand that specifically binds to the target substance, wherein the saccharide is chemically bound to the linker; a step for binding the ligand to the solid-phase carrier to obtain a solid-phase carrier having a ligand bound thereto; and a step for bringing the solid-phase carrier having the ligand bound thereto into contact with a sample containing the target substance that specifically binds to the ligand.

<2> A solid-phase carrier for capturing a target substance, the carrier having a base material, at least a portion of the surface thereof being formed of or coated with a saccharide, and having a linker of 5-100 atoms having a reactive functional group for binding a ligand that specifically binds to the target substance, wherein the saccharide is chemically bound to the linker.

<3> A method for producing a ligand bound solid-phase carrier for capturing a target substance, including a step of binding the solid-phase carrier according to <2> described above to a ligand.

<4> A ligand bound solid-phase carrier for capturing a target substance, produced by the production method according to <3> described above.

Advantageous Effects of Invention

According to the present invention, it is possible to provide a solid-phase carrier that has extremely low nonspecific adsorption of biological substances such as proteins, peptides, nucleic acids and cells, and is capable of maintaining the activity of bound ligands at a high level. Therefore, according to the method of the present invention for capturing a target substance, it is possible to efficiently capture the target substance.

Figure 1:
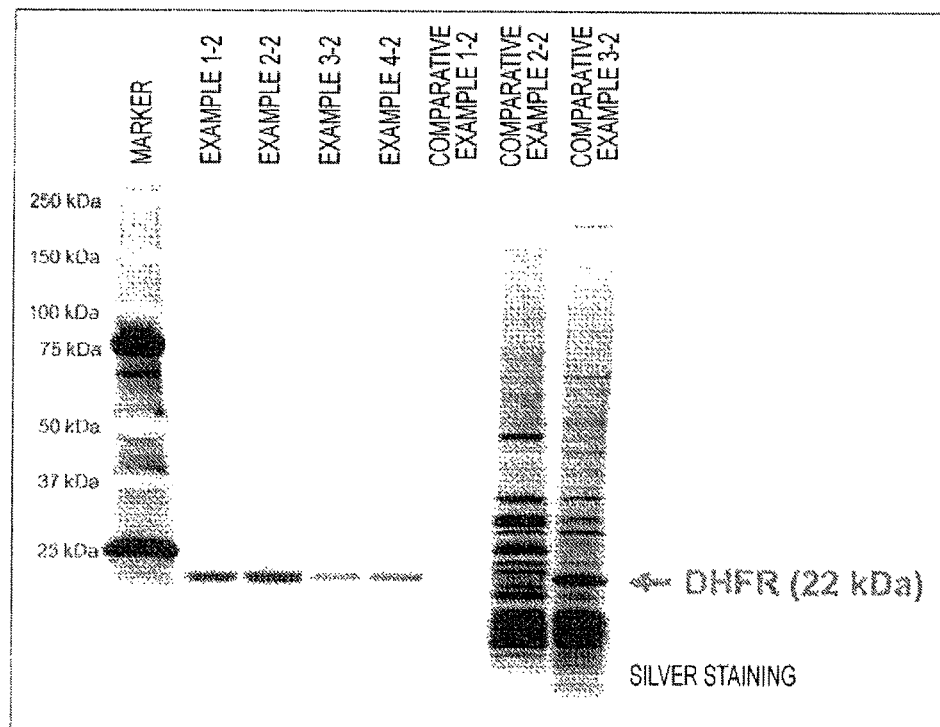
FIG. 1 shows the detection results of nonspecifically adsorbed proteins by the silver staining method.

DESCRIPTION OF EMBODIMENTS (Solid-Phase Carrier for Capturing Target Substance)

First, the solid-phase carrier for capturing a target substance according to the present invention (hereinafter, also simply referred to as the solid-phase carrier of the present invention) will be described in detail. It is to be noted that the description of "a to b" expressing the numerical range means "a or more and b or less", and it includs "a" and "b" within the range, unless otherwise specified in the present invention.

The solid-phase carrier of the present invention has a base material, at least a portion of the surface thereof being formed of or coated with a saccharide, and a linker of 5 to 100 atoms having a reactive functional group for binding a ligand that specifically binds to the target substance, in which the saccharide is chemically bound to the linker.

The solid-phase carrier of the present invention can be used as a carrier for ligand binding in the drug discovery/proteomics fields and diagnostic agents fields. For example, when a ligand is bound to a reactive functional group of the linker, the ligand is fixed to the base material, and it can be used in the analysis and/or measurement of the interaction using the intermolecular interactions between the ligand and the target substance (biological substances such as proteins), because of which selection/purification of a target substance become possible. Further, in addition to in the above drug discovery/proteomics fields and diagnostic field, applications of the solid-phase carrier of the present invention can also be expected in various fields, such as biochemistry, paints, papers, electrophotography, cosmetics, pharmaceuticals, agricultural chemicals, foods, catalysts.

<Base Material>

The base material in the present invention is one in which at least a portion of the surface thereof is formed of or coated with a saccharide. Here, the saccharide in the present invention means a concept including monosaccharides, disaccharides, trisaccharides or higher polysaccharides, and saccharides in which the functional group(s) is/are converted or modified. The saccharide may contain one kind thereof or may contain a combination of two or more thereof.

As a monosaccharide, it includes a triose, a tetrose, a pentose, and a hexose, among which a pentose and a hexose are preferable. Also, the monosaccharide may be an aldose or a ketose. Specific examples of the monosaccharide include xylose, ribose, deoxyribose, arabinose, fructose, glucose, mannose and galactose, for example. The disaccharide includes, for example, trehalose, lactose, kojiose, nigerose, maltose, isomaltose, sophorose, laminariose, cellobiose, and gentibiose. The polysaccharide other than the above disaccharides includes, for example, starch, amylose, amylopectin, dextran, dextrin, glycogen, cyclodextrin, cellulose, agarose, curdlan, alginic acid, inulin, glucomannan, chitin, chitosan, hyaluronic acid.

Furthermore, the saccharide in which at least a portion of the functional groups (such as a hydroxyl group, an amino group, and a carboxyl group) has been modified, such as carboxymethyl cellulose, carboxymethyl dextran, carboxymethyl starch, carboxymethyl chitin, and carboxymethyl curdlan, may be used. The modification may be made in multiple stages as needed.

In the present invention, polysaccharides are preferred as the saccharide. Further, such polysaccharides may be those wherein the functional group(s) may be converted or modified as described above. As such a polysaccharide, a high molecular weight polysaccharide is preferred from the viewpoint of coating efficiency in the case where the base material and the saccharide are chemically bound to cover the surface of the base material.

In addition, the saccharide in the present invention is preferably a saccharide having a carboxy group (preferably, a polysaccharide having a carboxyl group), and a partially carboxymethylated saccharide (preferably, a partially carboxymethylated polysaccharide) may be used. Specifically, such a saccharide includes preferably at least one selected from the group consisting of carboxymethyl cellulose, carboxymethyl dextran, carboxymethyl starch, carboxymethyl curdlan, hyaluronic acid and carboxymethyl chitin, and particularly preferably carboxymethyl cellulose.

Further, the carboxyl group content of the saccharide is preferably 0.1 to 2, more preferably 0.3 to 1.3, particularly preferably 0.5 to 0.9, per unit saccharide, in terms of an average carboxy group number.

The molecular weight of the saccharide is preferably 500 or more, more preferably 1000 or more, even more preferably 2000 or more, from the viewpoint of coating efficiency to the base material surface. From the viewpoint of suppressing the reduction in handling property and the decrease in coating efficiency associated with steric hindrance, the molecular weight of the saccharide is preferably 1000000 or less, more preferably 300000 or less, particularly preferably 100000 or less.

The shape of the base material is not particularly limited, and may include plate, film, filter, particulate, fibrous, hollow fiber, and monolithic shapes, among which a particulate shape is preferable. Further, magnetic particles containing a magnetic substance or a superparamagnetic substance are more preferable.

When the base material is in the form of particles, the volume average particle diameter of the base material (particle size) is preferably 0.1 to 20 μm, more preferably 0.3 to 17 μm, even more preferably 0.5 to 10 μm. When the particle diameter is 0.1 μm or more, separation efficiency using a magnetic separator, is enhanced to make it easy to separate particles and the washing solvent such as water, and thus removal of substances other than the target substance becomes highly efficient, leading to improved purification efficiency. On the other hand, by setting the particle diameter to 20 μm or less, a surface area can be sufficiently secured and thus the amount of captured target substance is increased.

The volume average particle diameter can be measured, for example, by a laser diffraction particle size distribution analyzer (SALD-200V, manufactured by Shimadzu Corporation.).

As the base material, there are exemplified a base material that is partially or entirely formed of a saccharide (agarose particles, cellulose particles or the like), a base material wherein at least a portion of the surface of an organic material or an organic-inorganic composite material other than saccharides, such as a sensor chip and magnetic particles, is coated with a saccharide, and a base material wherein at least a portion of the surface of an inorganic material such as a metal, silica, and silicon is coated with a saccharide. Please note that such coating with a saccharide may be either a physical coating or a chemical coating.

Among these base materials, a base material wherein at least a portion of the surface of an organic material or an organic-inorganic composite material is coated with a saccharide is preferable because of its excellent physical strength and chemical durability, and easy surface modification. More preferably, there is mentioned a base material wherein at least a portion of the surface of magnetic particles is coated with a saccharide. In addition the magnetic material contained in the magnetic particles may be any one of a ferromagnetic material, a paramagnetic material, and a superparamagnetic material, and it is preferably super-paramagnetic.

The internal composition of the magnetic particles may be homogeneous or heterogeneous, most of the homogeneous magnetic particles with a particle diameter in the above-mentioned range are paramagnetic. If repeatedly separated and purified by magnetism, the magnetic particles may lose their capability of being re-dispersed in a medium. For this reason, it is preferable that the magnetic particles have a heterogeneous internal composition containing fine particles of a magnetic material exhibiting small residual magnetization. At least one of $Fe_2O_3$ and $Fe_3O_4$ is preferable as the magnetic fine particles.

The inner structure of the magnetic particles having such a heterogeneous internal composition includes the following structures (i) to (iv):

(i) a structure in which magnetic fine particles are dispersed in a continuous phase of a non-magnetic material such as a polymer, (ii) a structure containing a secondary aggregate of fine particles of a magnetic material as a core and a non-magnetic material layer of a polymer or the like as a shell, (iii) a structure containing core particles (non-magnetic core particles) composed of a non-magnetic material such as a polymer, as a core, and a magnetic material layer (secondary aggregate materials of fine particles of a magnetic material) as a shell, and (iv) a structure containing mother particles having core particles composed of a non-magnetic material such as a polymer (non-magnetic core particles) and a magnetic layer provided on the surface of the core particles (secondary aggregate of magnetic fine particles) as a core, and a non-magnetic material layer such as a polymer provided on the outermost layer of the mother particles as a shell.

In addition, the polymer that can be used as a non-magnetic material that is not present in the outermost layer, such as non-magnetic core particles, may also be the same as the polymer described below as the polymer constituting the magnetic particles. Further, the magnetic material layer may include magnetic fine particles comprising at least one of $Fe_2O_3$ and $Fe_3O_4$.

In the present invention, among the above-mentioned structures (i) to (iv), the structure (iv) is preferred.

Further, any magnetic particles of the structures (i) to (iv) can be produced in accordance with a conventional method.

The magnetic particles of the structure (iii) may be produced by, for example, mixing the non-magnetic core particles with the magnetic material fine particles and allowing the magnetic material fine particles to be physically adsorbed on the surface of the non-magnetic material core particles. In the present invention, "physical adsorption" refers to an adsorption not involving a chemical reaction. The principle of "physical adsorption" includes, for example, hydrophobic/hydrophobic adsorption, molten bonding or adsorption, fusion bonding or adsorption, hydrogen bonding, and Van-der-Waals bonding. The magnetic particles of the structure (iii) above can also be prepared by a method utilizing hydrophobic/hydrophobic adsorption. For example, such a method includes a method comprising selecting non-magnetic core particles and magnetic material fine particles, each having a hydrophobic or hydrophobized surface, and dry-blending these non-magnetic core particles and magnetic material fine particles, and a method comprising sufficiently dispersing the non-magnetic core particles and magnetic material fine particles in a solvent (such as toluene or hexane) with good dispersibility without damaging both particles, followed by vaporization of the solvent while mixing.

Alternatively, the magnetic particles of the above structure (iii) may be produced by physically applying a strong external force to cause the magnetic material fine particles to be adsorbed on the surface of the non-magnetic material core particles. As examples of the method for physically applying a strong force, such a method includes a method using a mortar, an automatic mortar, or a ball mill; a blade-pressuring type powder compressing method; a method utilizing a mechanochemical effect such as a mechanofusion method; and a method using an impact in a high-speed air stream such as a jet mill, a hybridizer. In order to efficiently produce a firmly bound complex, a strong physical adsorption force is desirable. As such a method, there is exemplified a stirring method using a vessel equipped with a stirrer at a peripheral velocity of stirring blades of preferably 15 m/sec or more, more preferably 30 m/sec or more, and still more preferably from 40 to 150 m/sec. In addition, the magnetic particles of the above structure (iii) may also be obtained by suspension polymerization of the above vinyl monomer or polymer bulk pulverization. Specifically, the magnetic particles can be obtained by a two-stage swelling polymerization method using seed particles described in JP 57-24369 B, the polymerization method described in J. Polym. Sci., Polymer Letter Ed., 21,937 (1963), and the methods described in JP 61-215602 A, JP 61-215603 A, and JP 61-215604 A.

Further, the magnetic particles of the structure (iv) can be obtained, for example, by forming a non-magnetic material layer through a polymerization reaction or the like, on the surface of the magnetic particles of the structure (iii) obtained above as mother particles.

Vinyl polymers are preferable as the polymer constituting the magnetic particles used in the present invention.

As examples of the vinyl monomers constituting the vinyl polymer, there are exemplified aromatic vinyl monomers such as styrene, α-methylstyrene, halogenated styrene, and divinylbenzene; vinyl esters such as vinyl acetate and vinyl propionate; unsaturated nitriles such as (meth)acrylonitrile; ethylenically unsaturated carboxylic acid alkyl esters such as methyl (meth)acrylate, ethyl (meth)acrylate, butyl (meth)acrylate, 2-ethylhexyl (meth)acrylate, lauryl (meth)acrylate, and cyclohexyl (meth)acrylate; polyfunctional (meth)acrylates such as ethylene glycol di(meth)acrylate, and trimethylol propane tri(meth)acrylate; and (meth)acrylates having a functional group, such as glycidyl (meth)acrylate, and 2-hydroxyethyl (meth)acrylate; and (meth)acrylic acid, (meth)acrylamide, allyl (meth)acrylate, itaconic acid, N-methylol (meth)acrylamide, diallyl phthalate.

The vinyl polymer may be a homopolymer or a copolymer, and may also be a copolymer of the vinyl-based monomer and a conjugated diolefin such as butadiene, isoprene.

As the solid-phase carrier of the present invention, those in which a base material and a saccharide are chemically bound with each other are preferable. Particularly in the present invention, it is preferable to directly bind the functional group of the base material surface to the functional group contained in the saccharide, or it is preferable to combine these functional groups via a crosslinking agent. From the viewpoint of chemical stability, it is more preferable to perform the binding between these functional groups via a crosslinking agent.

As the crosslinking agent to be used in the present invention, its valency is preferably 2 to 6, more preferably 2 to 4, particularly preferably 2.

The functional group in the crosslinking agent is not particularly limited. Such a functional group includes, for example, a hydroxyl group, an acyl group, a mercapto group, an amino group, an aminoacyl group, a carbonyl group, a formyl group, a carboxyl group, an amide group, a sulfonic group, a phosphate group, an epoxy group, a tosyl group, an azido group, a vinyl group, and an allyl group.

Groups that are able to react with these crosslinking groups may be contained in the base material surface and the saccharide.

Further, bonding between a plurality of crosslinkable groups contained in the crosslinking agent is preferably formed with a hydrophilic polyvalent organic group such as a hydrocarbon group or a polyalkyleneoxy group. For example, in the present invention, when the base material surface has an epoxy group, it is preferable to use a crosslinking agent having an amino group as a crosslinkable group, such as ethylenediamine, 1,2-bis(aminoethoxy)ethane.

<Linker>

The solid-phase carrier of the present invention has a linker of 5-100 atoms having a reactive functional group for binding a ligand that specifically binds to a target substance. The linker used herein refers to a molecular chain that connects a base material to a ligand at a certain distance, when the ligand is bound to a reactive functional group.

The linker of 5-100 atoms in the present invention refers to a linker wherein the shortest distance between the saccharide ring structure and the ligand is regulated to the distance equivalent to 5-100 atoms when the ligand is bound to the saccharide. If the number of these atoms is less than 5, it is less likely to access the binding site of a target substance (proteins). On the other hand, if the number of the atoms exceeds 100, the reaction efficiency decreases when introducing the linker to the base material.

In the present invention, the number of the atoms is preferably 10 or more, more preferably 15 or more, even more preferably 20 or more, particularly preferably 25 or more, and preferably 80 or less, more preferably 70 or less, particularly preferably 60 or less, from the viewpoint of low nonspecific adsorption or from the viewpoint of target substance capturing capability.

Here, as mentioned above, the "number of atoms" of the linker in the present invention means the number of atoms when the ligand is bound to the linker and is intended to refer to the number of atoms counted from a starting point at the atom adjacent to the saccharide ring structure to an end point at the functional group to be used for the binding of the ligand (the portion remaining in the linker portion after binding of the ligand). For example, if a carboxymethyl cellulose is used as it is, the number of atoms as the linker is 4 from the starting carbon atom at 6-position up to the carbonyl carbon of the carboxy group, as shown in the following formula (1). Further, in the case of CMC-coated linker magnetic particles (A-5) of Example as mentioned below, the number of atoms as the linker is 14 as shown in the following formula (2). Also, if the linker has a ring structure or if the linker has a branched chain structure and has plural starting points and/or end points, the "number of atoms" refers to the minimum number of atoms from the starting point to the end point.

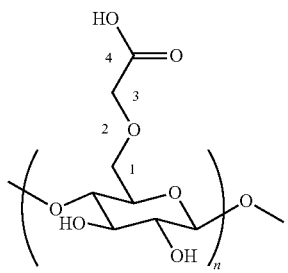

(1)

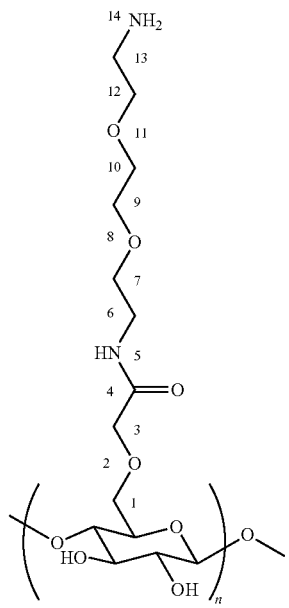

(2)

In the solid-phase carrier of the present invention, the linker is chemically bound to the saccharide, and the linker has a reactive functional group capable of chemically binding to a saccharide on at least one end, in addition to the reactive functional group described above, and is preferably bound to a saccharide with use of a molecule that forms a part or all of the linker (hereinafter, also referred to as a linker molecule).

The linker molecule used herein is preferably a molecule having reactive functional groups on at least two ends. When the ligand is directly bound to the base material without a linker, binding of the ligand to the target substance is prevented by factors such as steric hindrance, resulting in a possibility that the target substance is hardly captured. However, when the ligand is bound to the base material via a linker of 5-100 atoms, such fear is eliminated. Further, even when the ligand is bound to the base material via a linker, the ligand will be physically adsorbed on the surface of a base material and thus the activity of the ligand is reduced. However, since the base material surface of the solid-phase carrier of the present invention is coated with or formed of a saccharide, such solid-phase carrier has high hydrophilicity and can prevent the physical adsorption between the ligand and the base material, thereby to be able to remarkably suppress nonspecific adsorption.

The linker has preferably contains a hydrophilic structure in its structure. The operation for binding a ligand that is bound to a solid-phase carrier, to a target substance, is often carried out usually in an aqueous medium. In the case where the linker contains a hydrophilic structure, the linker takes easily a conformation in which molecular chains are extended in an aqueous medium, so that the function of the linker is likely to exert. Moreover, nonspecific adsorption of impurities other than the target substance contained in the sample is suppressed in such a case.

The hydrophilic molecular structure includes polyalkylene glycol chain, nucleic acid structure, polypeptide chain, polyhydroxyalkylene group, polyvinyl alcohol chain (including partially saponified polyvinyl acetate), polyvinyl methyl ether chain, poly-2-hydroxyethyl methacrylate chain, polyvinylpyrrolidone chain, polymer chains of acrylamide or acrylamide derivative, polyvinyl acetamide chain, polyvinyl formamide chain, glycosyl group, polysaccharide. Among these, one or two or more thereof may be contained in the hydrophilic molecular structure.

Of these, polyalkylene glycol chain, nucleic acid structure, polypeptide chain, polyhydroxyalkylene group, and glycosyl group are preferred; polyalkylene glycol chain, nucleic acid structure, and polypeptide chain are more preferred; and polyalkylene glycol chain is particularly preferred from the viewpoint of its high hydrophilicity and easy availability or synthesis.

As the polyalkylene glycol chain, there are exemplified a polyethylene glycol chain, a polypropylene glycol chain, a polyethylene glycol-polypropylene glycol diblock copolymer, and a polyethylene glycol-polypropylene glycol-polyethylene glycol ABA-type triblock copolymer (polyoxyethylene-polyoxypropylene-polyoxyethylene).

Moreover, the linker may contain a hydrophobic molecular structure such as an arylene group (e.g. phenylene group); a trivalent aromatic hydrocarbon group (e.g. benzenetriyl group); and an alkylene group (e.g. methylene group, ethylene group, propylene group), in addition to the hydrophilic molecular structure.

The structure of the main chain of the linker may be a linear structure or a branched structure (branching) such as star-type, comb-type or dendritic type, and a straight chain structure is preferred as the structure of the main chain of the linker.

The linker molecule preferably has a reactive functional group B that binds to the functional group of a saccharide, in addition to the reactive functional group A that binds to the ligand. The reactive functional group A and the reactive functional group B are preferably present in at least two ends of the main chain of the linker molecule. The reactive functional groups A and B of the linker may be the same with or different from each other.

If the main chain of the linker molecule is linear, such a linker preferably has the reactive functional group A and the reactive functional group B at each end. If the main chain of the linker molecule having a branched structure has a plurality of ends, at least two or more ends may have the reactive functional group A and the reactive functional groups B, and there may be an end having no reactive functional group.

The molecular weight of the linker molecule (number-average molecular weight) is not limited, as long as the molecular weight secures the length enough that the ligand and the base material are bonded at a sufficient distance thereby not to causing a steric hindrance in the binding with a target substance. Such a molecular weight is preferably about 200 to 4000, more preferably 1000 to 2500.

<Reactive Functional Group>

The linker has a reactive functional group for binding a ligand that specifically binds to a target substance. The reactive functional group (reactive functional group A of the linker molecule) is not limited as long as it can bind the ligand that specifically binds to a target substance, and includes, for example, a carboxy group, an amino group, a hydroxy group, an aldehyde group, a ketone group, an epoxy group, a mercapto group, a vinyl group, an allyl group, an acryl group, a methacryl group, a tosyl group, an azido group, an alkynyl group, an isocyanate group, an isothiocyanate group, a cyano group, and a halomethyl group, and may also include a photoreactive group such as arylazide, benzophenone, and trifluoromethyl phenyldiazirine. Among these, a carboxy group and an amino group are preferred, and a carboxyl group is more preferred.

Further, the reactive functional groups B of the linker molecule are the same as those described above.

The content of the reactive functional group for binding a ligand is preferably about 0.1 to 100 square Å/reactive functional group as a parking area, more preferably 1 to 50 square Å/reactive functional group, even more preferably 3 to 30 square Å/reactive functional group.

Here, the parking area refers to an index indicating the area occupied by the reactive functional groups of one molecule on the carrier surface. Generally, the ligand binding amount is inversely proportional to the numerical value of the parking area, and the ligand binding amount is reduced as the parking area becomes larger.

In addition, the content of the reactive functional groups for binding a ligand is preferably 1 μmol/g or more, more preferably 5 μmol/g or more, even more preferably 10 μmol/g or more, and preferably 400 μmol/g or less, more preferably 100 μmol/g or less, even more preferably 50 μmol/g or less, particularly preferably 30 μmol/g or less.

The content of the reactive functional groups for binding a ligand may be measured in accordance with the method described in Example.

<Active Functional Group>

The content of the active functional group is preferably 1 μmol/g or more, more preferably 5 μmol/g or more, even more preferably 10 μmol/g or more, particularly preferably 11 μmol/g or more, and preferably 100 μmol/g or less, more preferably 50 μmol/g or less, even more preferably 30 μmol/g or less, particularly preferably 15 μmol/g or less, from the viewpoint of target substance capturing performance.

Here, the active functional group in the present invention refers to a reactive functional group (i.e. a reactive functional group that is active and capable of binding to a ligand) that is used in the binding of a ligand, among the reactive functional groups for binding a ligand.

As a method for measuring the content of the active functional group, for example, chromatographic methods such as high performance liquid chromatography (HPLC) are mentioned. Specifically, when the reactive functional group is a carboxyl group or an amino group, the NHS amount liberated at the time of binding with the ligand may be quantified.

Further, from the viewpoint of target substance capturing performance, the content of the active functional groups is preferably 0.01% or more, more preferably 0.1% or more, even more preferably 0.5% or more, yet even more preferably 30% or more, furthermore preferably 45% or more, particularly preferably 55% or more, and is preferably 95% or less, more preferably 90% or less, particularly preferably 80% or less, in terms of 100% of the reactive functional group for binding a ligand. In addition, an increased ratio of the active functional groups makes the environment of the carrier surface hydrophobic generally under the influence of a hydrophobic ligand, so that a nonspecific binding tends to increase.

<Method for Producing Solid-Phase Carrier>

Next, a method for producing the solid-phase carrier of the present invention will be described.

The solid-phase carrier of the present invention can be produced, for example, by a step of binding a base material such as magnetic particles chemically to a saccharide so that at least a portion of the surface thereof is formed of or coated with a saccharide, and a step of binding the saccharide to the linker molecule chemically.

In the present invention, the known chemical reaction may be used as a means for chemically bonding the base material with the saccharide without any particular limitations. For example, the base material used for producing the solid-phase carrier of the present invention may have a plurality of functional groups (first functional group) on the surface. The first functional group may be a functional group introduced when the particle shape of the base material is formed or may be a functional group obtained by conversion after the formation of the particle shape of the base material. In that case, the conversion of the functional groups may be carried out two or more times as needed. For example, when the functional group introduced at the time of forming the particle shape of the magnetic particles is an epoxy group, an amino group produced by reacting the epoxy group with a large excess amount of ammonia or an appropriate diamine compound may be the first functional group, or when the functional group introduced at the time of forming the particle shape of the magnetic particles is a hydroxyl group, for example, an amino group produced by converting the hydroxyl group into a tosyl group and reacting the tosyl group with a large excess amount of an appropriate diamine compound may be the first functional group.

The saccharide used for producing the solid-phase carrier of the present invention may have a plurality of functional groups (second functional group) in one molecule, and such a functional group may be one that has been converted from the functional group of the saccharide.

As the functional group which can be used as the first functional group and/or the second functional group, there are exemplified a carboxyl group, a hydroxyl group, an epoxy group, an amino group, a mercapto group, a vinyl group, an allyl group, an acrylic group, a methacrylic group, a tosyl group, an azido group, an alkynyl group. In this case, combination of the first functional group and the second functional group should be a combination that is reactive with each other. When the first functional group is an epoxy group, for example, the second functional group may be an amino group, or when the first functional group is an amino group, for example, the second functional group may be a carboxyl group. It is possible to chemically bind the base material to the saccharide by reacting the first functional group and the second functional group directly or via a crosslinking agent.

Further, the chemical bond formation may be performed in the presence of the same solvent as in the ligand binding step.

Also, in the present invention, there is no particular limitation on the method for chemically bonding the saccharide and the linker molecule, and the known chemical reaction may be used for such purpose. For example, it is possible to chemically binding a saccharide to a linker molecule by chemical reaction between the functional group contained in the saccharide and the reactive functional groups B contained in the linker molecule.

The solid-phase carrier of the present invention is prepared in accordance with the above-described steps, and can be used as a solid-phase carrier after adjusting the pH and washing the surface by purification processing such as dialysis, ultrafiltration, and centrifugation, as needed.

[Method for Capturing Target Substance]

Next, the method for capturing target substance according to the present invention will be described below.

The method for capturing target substance according to the present invention is characterized by including a step of preparing a solid-phase carrier of the present invention (solid-phase carrier preparation step), a step of binding a ligand to the solid-phase carrier to obtain a solid-phase carrier having a ligand bound thereto (ligand binding step), and a step of bringing the solid-phase carrier having a ligand bound thereto into contact with a sample which may contain a target substance that specifically binds to the ligand (contact step).

<Ligand Binding Step>

The ligand binding step is a step for binding a ligand to a solid-phase carrier to obtain a solid-phase carrier having a ligand bound thereto.

The ligand used in the present invention is not particularly limited, and it includes, for example, proteins (e.g., antibodies, antigens, enzymes, receptors, hormones), peptides, nucleic acids (e.g. DNAs, RNAs), saccharide compounds, and chemicals (e.g. drug candidates). The solid-phase carrier of the present invention is suitable for binding of chemical substances, among the above-mentioned ligands. In particular, the solid-phase carrier is suitable for binding of water-insoluble compounds or binding of lipophilic compounds (especially lipophilic low molecular weight compounds).

Here, the water-insoluble compound refers to a compound having an amount of 1 g or less, preferably 0.1 g or less, dissolved in 100 mL of water at room temperature (20° C.).

Further, the lipophilic compound refers to a compound having a Log P value of −3.0 or more, preferably −2.0 or more, even more preferably 0 or more, which is a log value of octanol/water partition coefficient.

Specific examples of the ligand include, for example, methotrexate or its aminated derivatives (for example, MTX-NH2, manufactured by Tamagawa Seiki Co., Ltd.), and retinoic acid.

Binding of the ligand may be carried out in accordance with the conventional method, and, for example, such a method may be a covalent bond-forming method using a condensing reagent such as a carbodiimide.

For example, if the ligand is a protein, chemical bond between the ligand and the linker may be formed by reacting a functional group (e.g. amino group, carboxyl group) in the protein with a reactive functional group (e.g. carboxyl group, hydroxy group, amino group) of the linker. In this case, the ligand is bound to the linker via an amide bond or an ester bond.

Further, if the ligand is a nucleic acid, chemical bond formation between the ligand and the linker may be performed by reacting a functional group (e.g. phosphoric acid group) in the nucleic acid with a reactive functional group (e.g. hydroxy group) of the linker. In this case, the ligand is bound to the linker via a phosphodiester bond.

The ligand binding step is preferably carried out in a solvent. The solvent includes water; alcohols (e.g. methanol, ethanol, propanol, isopropyl alcohol, n-butyl alcohol, isobutyl alcohol, sec-butyl alcohol, t-butyl alcohol); ethylene glycol derivatives (e.g. ethylene glycol, ethylene glycol monomethyl ether, ethylene glycol monoethyl ether, ethylene glycol monopropyl ether, ethylene glycol monobutyl ether, ethylene glycol monoethyl ether acetate, diethylene glycol monomethyl ether, diethylene glycol monoethyl ether, diethylene glycol dimethyl ether, diethylene glycol diethyl ether); propylene glycol derivatives (e.g. propylene glycol, propylene glycol monomethyl ether, propylene glycol monoethyl ether, propylene glycol monopropyl ether, propylene glycol monobutyl ether, propylene glycol monomethyl ether acetate); ketones (e.g. acetone, methyl ethyl ketone, methyl isobutyl ketone, methyl amyl ketone, diisobutyl ketone, cyclohexanone); esters (e.g. ethyl acetate, butyl acetate, isobutyl acetate, ethyl lactate, γ-butyrolactone); amides (e.g. N,N-dimethylformamide, N,N-dimethylacetamide, N-methylpyrrolidone, hexamethylphosphoric triamide, 1,3-dimethyl-2-imidazoline, N,N'-dimethylpropylene urea, tetramethyl urea, N-methylpyrrolidone); sulfoxides (e.g. dimethyl sulfoxide); aromatic hydrocarbons (e.g. toluene, xylene, nitrobenzene); ethers (e.g. tetrahydrofuran, 1,3-dioxolane, diethyl ether, morpholine); halogenated hydrocarbons (e.g. chloroform, 1,2-dichloromethane); and nitromethane. These solvents may be used alone or in combination of two or more thereof.

Among them, from the viewpoint of dissolving a wide variety of physiologically active substances such as general drugs and candidates thereof, amides and sulfoxides are preferable, and N,N-dimethylformamide, hexamethylphosphoric triamide (HMPA), N-methylpyrrolidone (NMP), 1,3-dimethyl-2-imidazoline, and dimethyl sulfoxide are more preferable. The solid-phase carrier of the present invention is particularly suitable for the binding of water-insoluble compounds or lipophilic compounds in the solvent.

Further, water content of the solvent is preferably less than 50% by weight, more preferably less than 30% by weight.

Moreover, in the solid-phase carrier having a ligand bound thereto obtained in the ligand binding step, it is preferable that the ligand is chemically bound to the linker. The linker and the ligand are preferably bound via a chemical bond such as —O-bond, —S-bond, —S(=O)-bond, —S(=O)$_2$-bond, —C(=O)-bond, —C(=O)O-bond, —NR$^1$R$^2$-bond (wherein, R$^1$ and R$^2$ independently represent a hydrogen atom or an alkyl group such as a methyl group and an ethyl group), —NHC(=O)-bond, and —P(=O)$_2$-bond.

<Contacting Step>

The contacting step is a step for contacting a solid-phase carrier having a ligand bound thereto with a sample which may contain a target substance that specifically binds to the ligand. With such a step, the target substance is captured in the ligand.

The sample includes, for example, blood composition (e.g. whole blood, serum, plasma, blood components, various blood cells, blood clot, platelets); body fluids (e.g. urine, semen, breast milk, sweat, interstitial fluid, interstitial lymph, bone marrow fluid, tissue fluid, saliva, gastric juice, synovial fluid, pleural effusion, bile, ascites, amnion fluid); various liquids (e.g. microbial cell solution, cell culture media, cell culture supernatant, disrupted tissue cell suspension). The samples may be collected from a living body, or may be those that have been subjected to pretreatment.

In the present invention, the term "target substance" refers to a substance that is an objective to be captured and specifically binds to a ligand which is bound to the solid-phase carrier, and includes, for example, a biological substance. In the present invention, the biological substance refers to all biological substances related to biological bodies. As examples of the biological substance, there are exemplified substances contained in biological bodies, substances derived from substances contained in biological bodies, and substances that can be used in biological bodies. More specifically, the biological substance includes, but are not limited to, for example, proteins (such as an enzymes, antibodies, and receptors), peptides (such as glutathione and RGD peptides), nucleic acids (such as DNAs and RNAs), saccharides, lipids, and other cells and substances (such as various blood-originating substances containing various blood cells such as platelets, erythrocytes, and leukocytes, and various floating cells).

In the contacting step, the pH in the system is not particularly limited, and is generally within the range of pH 5 to 10, preferably in the range of pH 6 to 8. In order to maintain the pH of interest, typically, buffer solutions are used. As the buffer solution, for example, phosphoric acid, tris(hydroxy-methyl)aminomethane, HEPES, MES. are mentioned.

The reaction temperature of the contacting step is usually about 2 to 42° C., and the reaction time is usually about 5 minutes to one night.

If necessary, salts, proteins such as albumin, surfactants other than the nonionic surfactants mentioned above may be added to the reaction system of the contacting step. It is preferable not to add proteins or nucleic acids in view of subsequent analysis.

<Washing Step and Dissociation Step>

It is preferable that the method for capturing a target substance according to the present invention comprises a step for washing a composite of a solid-phase carrier and a target substance, produced in the contacting step (washing step), and a step for dissociating the target substance from the composite of a solid-phase carrier and a target substance (dissociation step).

The washing step for the composite and the dissociation step of the target substance from the composite may be performed in accordance with a conventional method.

(Washing Step)

For example, the washing step is usually divided into two types, depending on the shape of the solid-phase carrier. When the solid-phase carrier is particulate like magnetic particles, for example, there is exemplified a method of washing the magnetic particles by dispersing them in the washing solution, whereas when the solid-phase carrier is in the form like a microplate, there is exemplified a method for washing the microplate by contacting with a washing solution on its surface. Unreacted components and unreacted target substances are removed by the washing step.

Further, when the solid-phase carrier is magnetic particles, the washing step includes preferably a magnetism collecting step to separate magnetic particles and a liquid phase by collecting magnetic particles by a magnetic force, and a dispersion step to re-disperse the magnetic particles separated in the magnetism collecting step, in a liquid phase. As a result, unreacted substances and contaminants in the biological samples can be further efficiently washed, separated, and removed from the surface of magnetic particles. Specifically, such washing and separation may be performed by applying a magnetic field to the reaction vessel to collect magnetic particles by attaching them to the reaction vessel wall, removing the supernatant, further adding an appropriate washing solution thereto as needed, applying a magnetic field similarly, and repeating the operation of removing the supernatant.

(Dissociation Step)

Further, the target substance can be dissociated from the composite by using, for example, a reducing agent.

(Production Method of Ligand Bound Solid-Phase Carrier for Capturing Target Substance)

The production method of a ligand bound solid-phase carrier according to the present invention is characterized by including a step of binding the solid-phase carrier of the present invention to a ligand. The binding of the solid-phase carrier of the present invention to a ligand may be performed in a manner similar to the ligand binding step in the method for capturing a target substance according to the present invention.

EXAMPLES

Hereinafter, the present invention will be described in more detail by way of Examples. The present invention is not limited to these Examples. Further, in the Examples, "%" is expressed on a mass basis, unless otherwise specified.

<Evaluation of Physical Properties>

(Volume Average Particle Diameter)

The volume average particle diameter was measured by a laser diffraction particle size distribution analyzer (SALD-200V, manufactured by Shimadzu Corporation).

(Quantitative Determination of Amino Groups)

The amount of amino groups on the particle surface was quantified by using SPDP (manufactured by Dojindo Laboratories) according to the description of Journal of Biochemical and Biophysical Methods, 12, (1986), 349-354.

(Amount of Surface Functional Groups)

Using an aqueous dispersion containing 1 g (solid content) of particles, the amount of the surface functional groups (carboxyl groups) of the particles was determined by the difference between the apparent surface charge amount obtained by the conductivity titration described in JP 10-270233 A and the background charge amount obtained by using only a dispersion medium (water) in a similar measurement.

Synthesis Example 1

(Synthesis of Saccharide CMC-1)

20 g of carboxymethyl cellulose sodium (MP Biochemicals, low viscosity product (50 to 200 cps, 4% aqueous solution), etherification degree: 0.8) was dissolved in 300 mL of 0.1M aqueous sodium hydroxide solution, and the resulting solution was stirred for 1 hour. This solution was added dropwise to 3 L of isopropyl alcohol for reprecipitation. Thereafter, the resulting reprecipitate was air-dried and dried under vacuum to obtain 20.5 g of carboxymethyl cellulose (CMC-1).

Synthesis Example 2

(Synthesis of Amino Group-Supported Magnetic Particles (A-2))

2 g of 75% di(3,5,5-trimethylhexanoyl) peroxide solution ("Peroyl 355-75(S)" manufactured by NOF Corporation) and 20 g of 1% aqueous sodium dodecylsulfate solution were mixed, and the mixture was finely emulsified using an ultrasonic disperser. The resulting emulsion was added to a reactor charged with 13 g of polystyrene particles (volume average particle diameter of 0.77 µm) and 41 g of water, and the mixture was stirred at 25° C. for 12 hours. In another vessel, 96 g of styrene and 4 g of divinylbenzene were emulsified using 400 g of a 0.1% aqueous sodium dodecyl sulfate solution. This emulsion was added to the reactor. After stirring the mixture at 40° C. for 2 hours, the mixture was heated to 75° C. and polymerized for 8 hours. After cooling to room temperature, only particles were separated by centrifugation, washed with water, dried, and ground. The obtained particles were defined as core particles (a-1). The volume average particle diameter of the core particles (a-1) was 1.5 µm.

Then, acetone was added to an oily magnetic fluid ("EXP series" manufactured by Ferrotec Corporation) to precipitate particles, and the precipitated particles were dried to obtain ferrite-based magnetic fine particles (M-1) having a hydrophobized surface. The average primary particle diameter of the magnetic fine particles (M-1) was 0.02 µm.

Then, 15 g of the core particles (a-1) and 15 g of the magnetic fine particles (M-1) were thoroughly mixed using a mixer. The mixture was treated using a hybridization system ("NHS-0" manufactured by Nara Machinery Co., Ltd.) at a blade (stirring blade) peripheral velocity of 100 m/sec (16200 rpm) for 5 minutes to obtain particles (1) having a surface magnetic material layer formed of magnetic fine particles (M-1). The volume average particle diameter of the particles (1) was 2.0 µm.

Then, a 3 L-separable flask was charged with 1875 g of 0.5% aqueous solution of sodium dodecylbenzene sulfonate and then 75 g of the particles (1) was added to the flask. The mixture was dispersed using a homogenizer and the resulting dispersion was heated to 60° C. To 562.5 g of 0.5% aqueous sodium dodecylbenzene sulfonate solution were added 99 g of MMA (methyl methacrylate), 13.5 g of TMP (trimethylolpropane trimethacrylate) and 2.25 g of di(3,5,5-trimethyl-hexanoyl) peroxide (Peroyl 355, manufactured by NOF Corporation), and the mixture was finely dispersed using an ultrasonic disperser to prepare a pre-emulsion. The pre-emulsion was added dropwise over 2 hours to the 3 L-separable flask controlled at 60° C. After completion of the dropwise addition, the mixture was allowed to react for 1 hour while maintaining the temperature of the flask at 60° C.

Then, 32.06 g of MMA, 19.69 g of GMA (glycidyl methacrylate), 4.5 g of TMP, and 1.13 g of di(3,5,5-trimethylhexanoyl) peroxide (Peroyl 355, manufactured by NOF Corporation) were added to 281.25 g of 0.5% aqueous sodium dodecylbenzene sulfonate solution. The resulting mixture was finely dispersed using an ultrasonic disperser to obtain a pre-emulsion. The pre-emulsion was added dropwise over 1 hour and 20 minutes to the 3 L-separable flask controlled at 60° C. After heating the mixture to 75° C., the mixture was further polymerized for 2 hours and 20 minutes to complete the reaction. The resulting aqueous dispersion of the polymer coated-magnetic particles was subjected to magnetic purification and gravitational sedimentation purification to obtain an aqueous dispersion of magnetic particles (A-1) having a solid content concentration of 1%. The volume average particle diameter of the magnetic particles (A-1) was 2.9 µm.

The resulting aqueous dispersion 13.5 g of the magnetic particles (A-1) was weighed, and magnetically separated with a magnetic stand (Magical Trapper, manufactured by Toyobo Co., Ltd.) to remove the supernatant. After that, the magnetic particles were dispersed in 30 mL of dimethyl sulfoxide. Then, after performing magnetic separation and repeating an operation of washing with dimethyl sulfoxide three times, the magnetic particles were dispersed in 27 mL of dimethyl sulfoxide. After addition of 23 g of 1,8-diamino-3,6-dioxaoctane (DAD) thereto, the magnetic particles were heated for 24 hours with stirring at 50° C. under a nitrogen atmosphere. Thereafter, the supernatant was removed by magnetic separation, and the magnetic particles were washed five times with dimethyl sulfoxide and five times with distilled water to obtain 13.5 g of amino group-supported magnetic particles (A-2) as an aqueous dispersion. The amount of the amino groups on the surface of the magnetic particles (A-2) was 183 µmol/g by the determination using SPDP.

Example 1-1

(Synthesis of CMC-Coated Linker Magnetic Particles Having Linker Length of 27 Atoms (A-7))

N,N-Dimethyl(4,6-diazaocta-4,5-dien-1-yl)amine monohydrochloride (3.2 g) and N-hydroxysuccinimide (2 g) were added to 2.5% aqueous solution in which 10 g of CMC-1 obtained in Synthesis Example 1 was dissolved, and the mixture was mixed by inversion at room temperature for 15 minutes. Subsequently, 3 g of the amino group-supported magnetic particles (A-2) obtained in Synthesis Example 2 was added thereto, and the mixture was mixed by inversion at room temperature for 20 hours. Thereafter, the supernatant was removed by magnetic separation, and the particles were dispersed in pure water, subjected to magnetic separation, and washed 5 times repeatedly. After that, the particles were dispersed in pure water again to measure the weight of the solid content, thereby to obtain 3.0 g of CMC-coated magnetic particles (A-3) as an aqueous dispersion.

Next, magnetic separation and washing of 3.0 g of the CMC-coated magnetic particles (A-3) dispersed in pure water were repeated 5 times and the particles were dispersed in 15 mL of 1,3-dioxolane. After the dispersion was cooled to 0° C. in an ice bath, 7.5 mL of acetic anhydride was slowly added and the mixture was mixed by inversion at room temperature for 3 hours. Then, the supernatant was removed by magnetic separation and the particles were washed 3 times with 1, 3-dioxolane and 5 times with pure water. To these particles was added 20 mL of 0.1M aqueous sodium hydroxide solution, and the mixture was dispersed by inversion mixing at room temperature for 30 minutes. After completion of the reaction, the supernatant was removed by magnetic separation, and the particles were washed 5 times with pure water and dispersed in 15 mL of pure water again to measure the weight of the solid content, thereby to obtain 3.0 g of CMC-coated magnetic particles (A-4) as an aqueous dispersion.

The dispersion medium of the resulting CMC-coated magnetic particles (A-4) was replaced with 30 mL of dimethylformamide with a dehydrated grade (dehydrated DMF) by repeating washing process and magnetic separation 5 times. After this medium was cooled to 0° C. in an ice bath, 1670 mg of (dimethyl-amino)morpholino[[(1-cyano-2-oxo-2-ethoxy-ethylidene)amino]oxy]methyl cation hexafluorophosphate (COMU) and 1345 μL of N,N-diisopropylethylamine (DIEA) were added thereto. The resulting mixture was mixed by inverse at room temperature for 15 minutes. Then, 1150 μL of DAD was added and the mixture was allowed to react while inversely mixing at room temperature for 18 hours. After completion of the reaction, the supernatant was removed by magnetic separation, and the particles were washed 3 times with DMF and 5 times with pure water, and dispersed again in 15 mL of pure water. After that, the weight of the solid content was measured to obtain 3.0 g of CMC-coated linker magnetic particles (A-5) as an aqueous dispersion.

Then, the dispersion medium of the CMC-coated magnetic particles (A-5) was replaced with 15 mL of dehydrated DMF by repeating washing process and magnetic separation 5 times. To this was gently added a 15 mL DMF solution containing 1570 mg of COMU, 1260 μL of DIEA, and 1410 μL of α-carboxymethyl-ω-carboxymethoxy-polyoxyethylene (average molecular weight: 250, manufactured by Sigma-Aldrich Corp.), which had been prepared in an ice bath and had been inversely mixed at room temperature for 15 minutes. The resulting mixture was allowed to react while inversely mixing at room temperature for 18 hours. After completion of the reaction, the supernatant was removed by magnetic separation and the particles were washed 3 times with DMF and 5 times with pure water, and dispersed again in 15 mL of pure water. After that, the weight of the solid content was measured to obtain 3.0 g of CMC-coated linker magnetic particles (A-6) as an aqueous dispersion.

Then, the dispersion medium of the CMC-coated linker magnetic particles (A-6) was replaced with 15 mL of 1,3-dioxolane by repeating washing and magnetic separation 5 times. After this medium was cooled to 0° C. in an ice bath, 7.5 mL of acetic anhydride was slowly added thereto, and the resulting mixture was inversely mixed at room temperature for 3 hours. Thereafter, the supernatant was removed by magnetic separation and the particles were washed with 1, 3-dioxolane 3 times and with pure water 5 times, and 20 mL of 0.1M aqueous sodium hydroxide solution was added to the particles. The mixture was inversely mixed at room temperature for 30 minutes. After completion of the reaction, the supernatant was removed by magnetic separation, and the particles were washed with pure water 5 times and dispersed again in 15 mL of pure water. After that, the weight of the solid content was measured to obtain 3.0 g of CMC-coated linker magnetic particles having a linker length of 27 atoms (A-7) as an aqueous dispersion. The amount of the surface functional groups of the particles (A-7) was 20 μmol/g.

Example 1-2

With respect to the particles (A-7) obtained in Example 1-1, the binding of the ligand and the active carboxylic acid content were measured. Further, by using a material (particles (A-8)) obtained by binding a ligand to the particles (A-7), an experiment to capture a target protein from a cell lysate solution was performed to evaluate specific capturing ability. A specific procedure is shown in the following.
(Ligand Binding Reaction)

An aqueous dispersion of the CMC-coated linker magnetic particles (A-7) obtained in Example 1-1 was weighed in an amount of 3 mg in terms of a solid content, and magnetic separation was performed with a magnetic stand to remove the supernatant. After washing 3 times with dehydrated DMF, the particles were suspended in 540 μL of DMF, and the suspension was allowed to stand on ice. To this were added 30 μL of 0.1 mol/L DMF solution of 1-ethyl-3-(3-dimethylamino-propyl)carbodiimide hydrochloride (EDC) and 30 μL of 0.1 mol/L DMF solution of N-hydroxysuccinimide (NHS), and the mixture was inversely mixed for one hour. Then, the particles were washed with 600 μL of dehydrated DMF three times and suspended in 580 μL of dehydrated DMF. To the suspension was added 20 μL of DMF solution of 0.01 mol/L methotrexate aminated derivative (MTX-NH2: manufactured by Tamagawa Seiki Co., Ltd.), and the mixture was allowed to react by inverse mixing at 4° C. for one hour. After completion of the reaction, magnetic separation was performed to collect the supernatant (Note that the collected supernatant in this treatment was used for the measurement of active carboxylic acid content). Thereafter, the particles were washed with DMF 3 times and with DMF 5 times, and re-suspended in 600 μL of pure water to obtain, as an aqueous dispersion, particles (A-8) formed by binding a ligand to the CMC-coated linker magnetic particles.

The structure of the linker of the particles (A-8) is shown below.

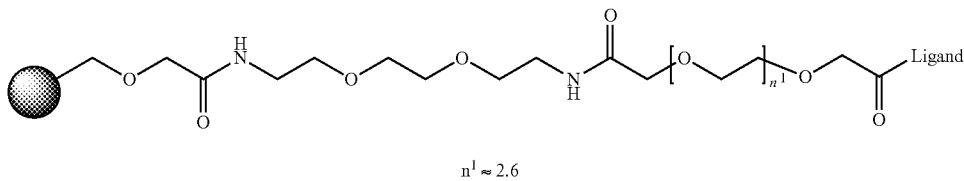

n¹ ≈ 2.6

(Measurement of Active Carboxylic Acid Content)

The reaction supernatant collected in the ligand binding step was used as a sample, and the amount of the liberated NHS contained therein was quantified by HPLC, thereby to evaluate the active carboxylic acid content of the particles (A-7) (ligand binding amount). A calibration curve was prepared within the range of 0.5 to 100 μM and subsequently active carboxylic acid content was evaluated by measuring an absorbance (wavelength: 260 nm) of the sample. As a result, the active carboxylic acid content was 12.0 μmol/g.

The HPLC conditions are shown below.

Apparatus: LC-2000 series, manufactured by JASCO.

Column: Inertsil ODS3 (manufactured by GL Sciences Inc., 150 mm×3.0 mm)

Mobile phase: 10 mM ammonium acetate buffer solution (pH 5.7) (mobile phase A) and acetonitrile (mobile phase B), 0 to 20 minutes: gradient conditions of A94%, B6%→A60%, B40% (linear gradient).

(Protein Binding Reaction)

First, a buffer (pH 7.9) having the following composition (hereinafter, referred to as buffer (A)) was prepared.

Composition of buffer (A): HEPES: 20 mM, glycerol: 10% (v/v), KCl: 0.1 M, EDTA: 0.2 mM, dithiothreitol (DTT): 1 mM.

Then, 3 mg of the ligand-bound particles (A-8) was washed with 400 μL of buffer (A) 3 times, dispersed in 300 μL of buffer (A), and allowed to stand on ice. A buffer (A) dispersion (300 μL) of previously prepared RAW 264.7 cell lysate solution ($1.5 \times 10^7$ cells) was added to the above dispersion. The mixture was incubated at 4° C. for 4 hours. It is to be noted that dehydrofolate reductase (DHFR: 22 kDa) that is a target protein is contained in the above-mentioned cell lysate solution. After completion of the reaction, the particles were collected by magnetic separation to remove the supernatant with use of a magnetic stand, and washed repeatedly with the buffer (A) 5 times to obtain target protein-bound particles (A-9).

(Detachment of Protein)

A sample for SDS-PAGE was prepared by adding 10 μL of an LDS sample buffer (NuPAGE LDS Sample Buffer (4×), manufactured by Life Technologies Co., Ltd.) and 30 μL of a reducing reagent (NuPAGE Sample Reducing Agent (10×), manufactured by Life Technologies Co., Ltd.) into a tube containing 3 mg of the target protein-bound particles (A-9), and heating the mixture for 5 minutes at 95° C. in a tube heater, so that the target protein-bound to the ligand-bound particles was detached therefrom.

(Evaluation of Protein Bound to Particles)

The above sample was applied to 7.5 to 15% gradient gel for SDS-PAGE so as to be a concentration of 6 μL/lane, and SDS-PAGE was performed.

Thereafter, the separated proteins were detected by the silver staining method and the Western-Blotting method.

The silver staining method was performed using 2D-silver staining reagent-2 (manufactured by Cosmo Bio Co., Ltd.) in accordance with the protocol attached. The results are shown in FIG. 1.

Figure 2:
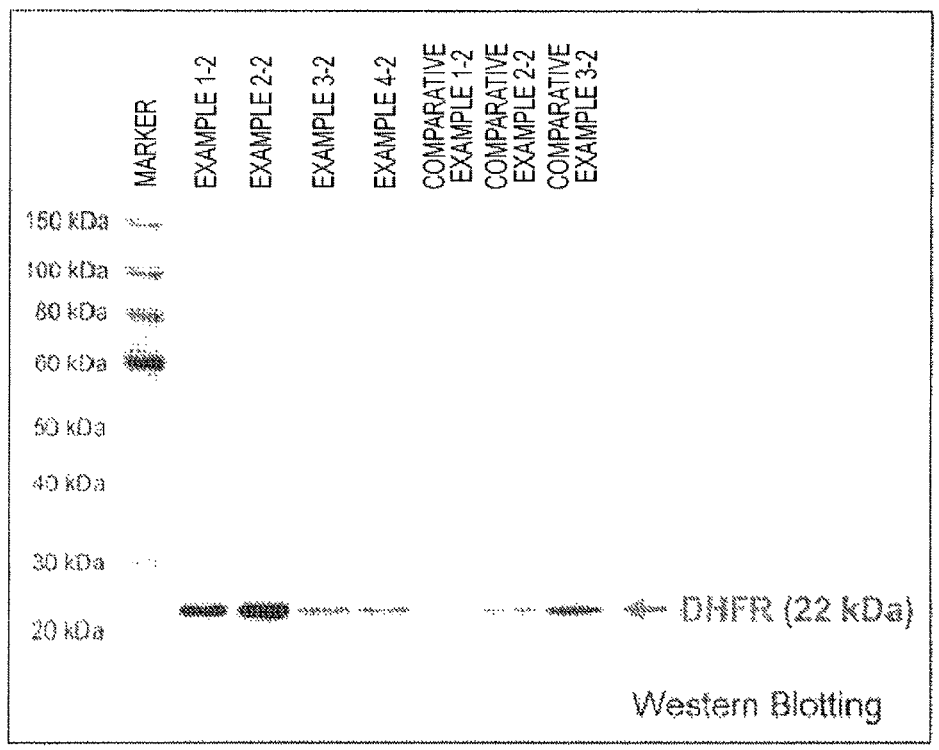
FIG. 2 shows the detection results of DHFR by the Western-Blotting method.

The Western-Blotting method was carried out in the following procedure: (1) Separation gel was transferred to a membrane (Trans-Blot Turbo Transfer Pack Midi format, 0.2 μm PVDF, manufactured by BIO-RAD Co., Ltd.), and the membrane was shaken in a blocking agent (BlockingOne, manufactured by Nacalai Tesque, Inc.) for 1 hour at 25° C.; (2) Further, after washing the membrane with a washing liquid (TBS containing 0.05% Tween 20), 1 μg/mL of a primary antibody was added to the membrane and shaken for 1 hour at 25° C.; (3) The membrane was washed with the washing liquid, and 0.5 μg/mL HRP-labeled anti-mouse IgG antibody as a labeled antibody (Mouse True Blot ULTRA, manufactured by Rockland, Inc.) was added thereto and shaken for 1 hour at 25° C.; and (4) Further, after washing the membrane with the washing liquid, a luminescent substrate (SuperSignal West Dura Chemiluminescent Substrate, manufactured by Thermo Scientific Inc.) was allowed to react. Then, bands were detected with a chemiluminescence detection system. The results are shown in FIG. 2.

The detection of nonspecifically adsorbed proteins by the above-mentioned silver staining method, and the detection of DHFR by the Western-Blotting method were carried out respectively. Further, the detection results were evaluated according to the following criteria. The results are shown in Table 1.

[Evaluation Criteria of Capture Amount of Target Protein]

4: a remarkably dark band was detected in the Western-Blotting method.

3: a dark band was detected in the Western-Blotting method.

2: a pale band was detected in the Western-Blotting method.

1: a slightly confirmed band was detected in the Western-Blotting method.

[Evaluation Criteria of Nonspecifically Adsorbed Protein Amount]

3: nonspecific adsorption of proteins was hardly observed in the silver staining method.

1: nonspecific adsorption of proteins was significantly observed in the silver staining method.

Example 2-1

(Synthesis of CMC-Coated Linker Magnetic Particles Having Linker Length of 51 Atoms (A-10))

CMC-coated linker magnetic particles (A-10) 3.0 g having a linker length of 51 atoms were obtained as an aqueous dispersion in the same manner as in Example 1-1, except for using α-carboxymethyl-ω-carboxylmethoxy-polyoxyethylene (manufactured by Sigma-Aldrich Corp., average molecular weight: 600) in place of α-carboxymethyl-ω-carboxymethoxy-polyoxyethylene (manufactured by Sigma-Aldrich Corp., average molecular weight: 250) used in the preparation of particles (A-6). The amount of the surface functional groups of the particles (A-10) was 19 μmol/g.

Example 2-2

The procedures of (1) ligand binding reaction, (2) measurement of active carboxylic acid content, (3) protein binding reaction, (4) detachment of proteins, and (5) evaluation of proteins bound to particles, were evaluated in the same manner as in Example 1-2, except for changing particles (A-7) to particles (A-10). The results are shown in Table 1 and FIGS. 1 and 2.

Further, the structure of the linker in the particles obtained by binding the ligand to the particles (A-10) is as shown below.

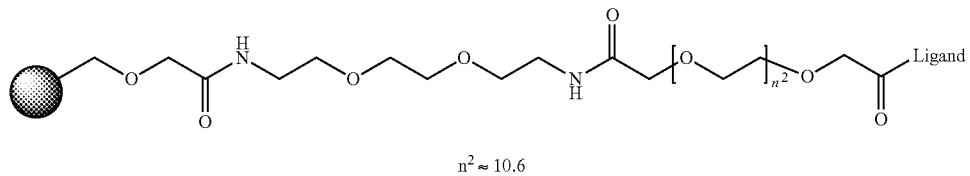

$n^2 \approx 10.6$

Example 3-1

(Synthesis of CMC-Coated Linker Magnetic Particles (A-11) Having Linker Length of 18 Atoms)

The CMC-coated linker magnetic particles (A-5) obtained in the same manner as in Example 1-1 were washed with 1,3-dioxolane and the particles were magnetically separated. After repeating this operation twice, the particles were dispersed in 15 mL of 1,3-dioxolane. After addition of 0.2 g of triethylamine and 0.5 g of succinic anhydride to the dispersion, the mixture was stirred at room temperature for 4 hours. After completion of the reaction, the supernatant was removed by magnetic separation, and the particles were washed with 1,3-dioxolane 3 times and with pure water 5 times. Then, the particles were re-dispersed in 15 mL of pure water again, and the weight of the solid content was measured to obtain 3.0 g of CMC-coated linker magnetic particles (A-11) having a linker length of 18 atoms as an aqueous dispersion. The amount of the surface functional groups of the particles (A-11) was 19 µmol/g.

Example 3-2

The following procedures: (1) ligand binding reaction, (2) measurement of active carboxylic acid content, (3) protein binding reaction, (4) detachment of proteins, and (5) evaluation of proteins bound to particles, were carried out in the same manner as in Example 1-2, except for changing particles (A-7) to particles (A-11). The results are shown in Table 1 and FIGS. 1 and 2.

Further, the structure of the linker in the particles obtained by binding the ligand to the particles (A-11) is as shown below.

Example 4-1

(Synthesis of CMC-Coated Linker Magnetic Particles (A-12) Having Branched Linker Length of 41 Atoms)

First, a compound represented by the following formula (branched linker compound) was synthesized with reference to the description of WO 2004/025297.

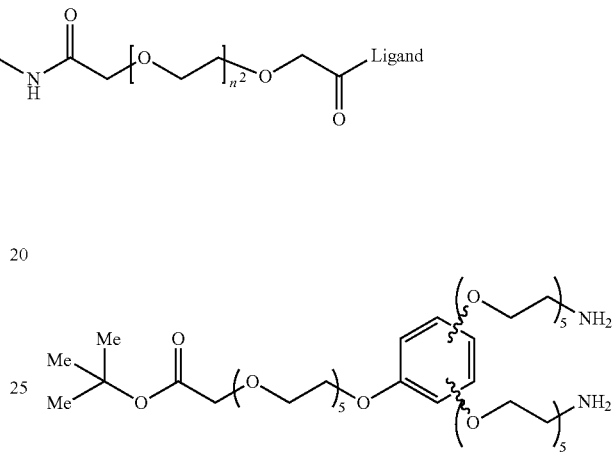

Then, an aqueous dispersion containing 3.0 g of CMC-coated magnetic particles (A-4) was obtained in the same manner as in Example 1-1, and the dispersion medium was replaced by 30 mL of dehydrated DMF by repeating magnetic separation and washing 5 times. After cooling to 0° C. in an ice-bath, 1670 mg of COMU and 1345 µL of DIEA were added to the particles and the mixture was subjected to inverse mixing at room temperature for 15 minutes. Then, 3170 µL of the synthesized branched linker compound was added thereto and the reaction was carried out at room temperature for 18 hours with inverse mixing. After completion of the reaction, the supernatant was removed by magnetic separation, and the particles were washed with DMF 3 times and with pure water 5 times. Thereafter, 15 mL of 5% aqueous trifluoroacetic acid solution was added thereto and the mixture was stirred at room temperature for 30 minutes to conduct a deprotection of the t-Boc group used for the protection of the carboxyl group. After completion of the reaction, the supernatant was removed by magnetic separation, and the particles were washed with pure water 5 times. The particles were dispersed in 15 mL of pure water again to measure the weight of the solid content, thereby to obtain 3.0 g of CMC-coated branched linker magnetic particles (A-12) as an aqueous dispersion. The amount of the surface functional groups of the particles (A-12) was 35 µmol/g.

Example 4-2

The following procedures: (1) ligand binding reaction, (2) measurement of active carboxylic acid content, (3) protein

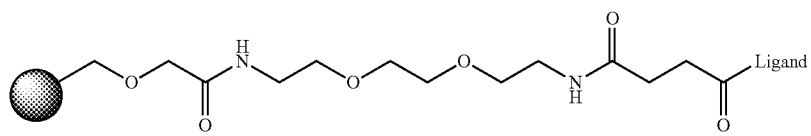

binding reaction, (4) detachment of proteins, and (5) evaluation of proteins bound to particles were carried out in the same manner as in Example 1-2, except for changing the particles (A-7) to the particles (A-12). The results are shown in Table 1 and FIGS. 1 and 2.

Further, the structure of the linker in the particles obtained by binding the ligand to the particles (A-12) is as shown below.

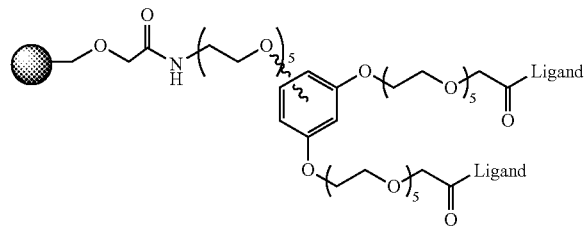

Comparative Example 1-1

The CMC-coated magnetic particles (A-4) synthesized in Example 1-1 were used as particles of Comparative Example 1-1. The CMC-coated magnetic particles (A-4) are CMC-coated linker magnetic particles having a linker length of 4 atoms. The amount of the surface functional groups of the particles (A-4) was 26 μmol/g.

Comparative Example 1-2

The following procedures: (1) ligand binding reaction, (2) measurement of active carboxylic acid content, (3) protein binding reaction, (4) detachment of proteins, and (5) evaluation of proteins bound to particles, were carried out in the same manner as in Example 1-2, except for changing the particles (A-7) to the particles (A-4). The results are shown in Table 1 and FIGS. 1 and 2.

Further, the structure of the linker in the particles obtained by binding the ligand to the particles (A-4) is as shown below.

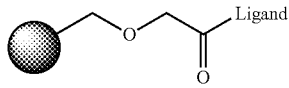

Comparative Example 2-1

(Synthesis of Organic Polymer-Coated Magnetic Particles Having Linker Length of 10 (B-3)

Into a 7 L-separable flask was poured 4250 g of 0.5% aqueous sodium dodecylbenzene sulfonate solution, and then 170 g of the particles (1) having a magnetic layer on the surface obtained in Synthesis Example 2 was added thereto. The mixture was dispersed with a homogenizer and heated to 60° C. A pre-emulsion prepared by adding 229.5 g of MMA (methyl methacrylate), 25.5 g of TMP (trimethylolpropane methacrylate) and 5.1 g of di(3,5,5-trimethylhexanoyl)peroxide (Peroyl 355, manufactured by NOF Corporation) to 1275 g of 0.5% aqueous sodium dodecylbenzene sulfonate solution, and finely dispersing the mixture with an ultrasonic disperser, was dropwise added over 2 hours to the 7 L-separable flask controlled at 60° C. After the dropwise addition, the mixture was allowed to react with stirring for 1 hour while maintaining the temperature of the flask at 60° C.

Then, 111.56 g of GMA (glycidyl methacrylate), 15.94 g of TMP and 2.55 g of di(3,5,5-trimethylhexanoyl) peroxide (Peroyl 355, manufactured by NOF Corporation) were added to 637.5 g of 0.5% aqueous sodium dodecylbenzene sulfonate solution. The resulting mixture was finely dispersed using an ultrasonic disperser to obtain a pre-emulsion. The pre-emulsion was added dropwise to the 7 L-separable flask controlled at 60° C. over 1 hour and 20 minutes. Thereafter, the mixture was heated to 75° C., and further polymerized for 2 hours and 20 minutes to complete the reaction. The resulting aqueous dispersion of the polymer coated-magnetic particles was purified by magnetic separation and gravitational sedimentation to obtain an aqueous dispersion of magnetic particles (B-1) having a solid content concentration of 1%. The volume average particle diameter of these magnetic particles (B-1) was 2.9 μm.

The resulting magnetic particles (B-1) (200 g) and water (1800 mL) were placed in a 3 L-separable flask, and 222 mL of 1 mol/L aqueous sulfuric acid solution was added thereto. The mixture was stirred at 60° C. for 6 hours. Then, the particles in the above separable flask were subjected to magnetic separation, and repeatedly washed with distilled water to obtain magnetic particles (B-2) having 2,3-dihydroxypropyl groups. The volume average particle diameter of these magnetic particles (B-2) was 2.9 μm.

The magnetic particles (B-2) (200 g) were washed with 500 mL of 1,3-dioxolane L and subjected to magnetic separation. After repeating this operation twice, the particles were dispersed in 1070 mL of 1,3-dioxolane. Triethylamine (29 g) and succinic anhydride (200 g) dissolved in 1026 g of 1,3-dioxolane were added to the above dispersion, and the mixture was stirred at room temperature for 4 hours. After completion of the reaction, the particles were magnetically separated, washed twice with 1,3-dioxolane, 3 times with acetone, and then 4 times with distilled water, to obtain organic polymer coated-magnetic particles (B-3) with a linker length of 10 having a carboxy group. The volume average particle diameter of the particles (B-3) was 2.9 μm and the amount of the surface functional groups was 21 μmol/g.

Comparative Example 2-2

The following procedures: (1) ligand binding reaction, (2) measurement of active carboxylic acid content, (3) protein binding reaction, (4) detachment of proteins, and (5) evaluation of proteins bound to particles were carried out in the same manner as in Example 1-2, except for changing the particles (A-7) to the particles (B-3). The results are shown in Table 1 and FIGS. 1 and 2.

Further, the structure of the linker in the particles obtained by binding the ligand to the particles (B-3) is as shown below.

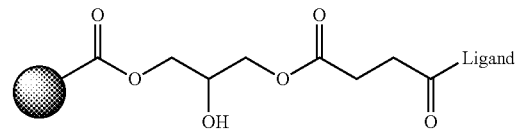

Comparative Example 3-1

Commercially available organic polymer coated-magnetic particles for capturing a target protein (FG-beads COOH beads, manufactured by Tamagawa Seiki Co., Ltd.) were used as particles of Comparative Example 3-1. These particles were defined as particles (B-4). The particles (B-4) have a volume average particle diameter of 200 to 250 nm, and the content of carboxyl groups is 200 to 250 µmol/g (both are based on catalog values).

Comparative Example 3-2

The following procedures: (1) ligand binding reaction, (2) measurement of active carboxylic acid content, (3) protein binding reaction, (4) detachment of proteins, and (5) evaluation of proteins bound to particles, were carried out in the same manner as in Example 1-2, except for changing the particles (A-7) to the particles (B-4). The results are shown in Table 1 and FIGS. 1 and 2.

Further, the structure of the linker in the particles obtained by binding the ligand to the particles (B-4) is as shown below.

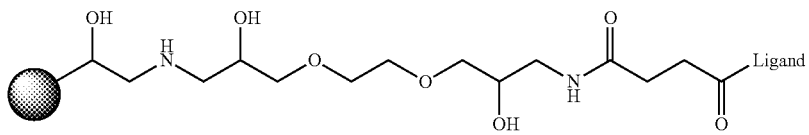

polymer coated-particles produced in Comparative Example 2-1, a lot of nonspecifically adsorbed proteins were observed, and moreover, the amount of the captured target proteins was small. The particles of Comparative Example 3-1 showed a high active carboxylic acid value (although the same degree as the density of carboxylic acids) because such particles have a small value of a particle size of 200 to 250 nm which is about 1/10 of the particles of Example, and a lot of nonspecifically adsorbed proteins were observed.

The invention claimed is:
1. A method for capturing a target substance, comprising:
preparing a solid-phase carrier for capturing a target substance, the carrier having a base material which is a particle having a particle diameter of from 0.5 to 10 µm, at least a portion of the surface thereof being formed of or coated with a saccharide, and having a linker comprising a polyalkylene glycol chain in a structure thereof and having a reactive functional group for binding a lipophilic ligand that specifically binds to the target substance and that has a Log P value of 0 or more, the Log P value being a log value of an octanol/

TABLE 1

|  | Example 1-1 Example 1-2 | Example 2-1 Example 2-2 | Example 3-1 Example 3-2 | Example 4-1 Example 4-2 | Comparative Example 1-1 Comparative Example 1-2 | Comparative Example 2-1 Comparative Example 2-2 | Comparative Example 3-1 Comparative Example 3-2 |
|---|---|---|---|---|---|---|---|
| Particles (Before ligand binding) | (A-7) | (A-10) | (A-11) | (A-12) | (A-4) | (B-3) | (B-4) |
| Particle surface coating | CMC | CMC | CMC | CMC | CMC | Organic polymer | Organic polymer |
| Linker length (Number of atoms) | 27 | 51 | 18 | 41 | 4 | 10 | About 18 |
| Amount of surface functional group (µmol/g) | 20 | 19 | 19 | 35 | 26 | 21 | 200-250 |
| Amount of active carboxylic acid (µmol/g) | 12.0 | 12.8 | 10.2 | 18.6 | 1.9 | 10.6 | 67 |
| Amount of captured target protein | 4 | 4 | 2-3 | 2-3 | 1 | 2 | 3 |
| Amount of nonspecifically adsorbed protein | 3 | 3 | 3 | 3 | 3 | 1 | 1 |

Organic polymer: (Meth)acrylic polymer:

When using the particles prepared in Examples 1-1 and 2-1, nonspecifically adsorbed proteins derived from the cell lysate solution were hardly found (evaluation of amount of nonspecifically adsorbed protein: "3"), and it found that a target protein DHFR was captured very efficiently (evaluation of amount of captured target protein: "4"). Also, in the case of using the particles produced in Example 3-1 and 4-1, nonspecifically adsorbed proteins were hardly found (evaluation of amount of nonspecifically adsorbed protein: "3") and DHFR was found to be efficiently captured (evaluation of amount of captured target protein: "2" to "3").

On the other hand, in the case of using the particles of Comparative Example 1-1, the value of the active carboxylic acid amount is small, and the captured target proteins were not almost observed. Further, in the case of using the organic water partition coefficient, wherein the number of atoms of the linker is 20-100, provided that the number of atoms of the linker is the number of atoms when the lipophilic ligand is bound to the linker and is the number of atoms counted from a starting point at the atom adjacent to the saccharide ring structure to an end point at the reactive functional group to be used for the binding of the lipophilic ligand, and that when the linker has a ring structure or the linker has a branched chain structure and has plural starting points and/or end points, the number of atoms of the linker is the minimum number of atoms from the starting point to the end point, and the saccharide is chemically bound to the linker;

binding the lipophilic ligand to the solid-phase carrier to obtain a solid-phase carrier having a ligand bound thereto; and bringing the solid-phase carrier having the ligand bound thereto into contact with a sample possibly containing the target substance that specifically binds to the lipophilic ligand.

2. The method according to claim 1, wherein the base material is one in which at least a portion of the surface of magnetic particles is coated with a saccharide.

3. The method according to claim 1, wherein the linker further comprises in the structure thereof at least one structure selected from the group consisting of a nucleic acid structure and a polypeptide chain.

4. The method according to claim 1, wherein the reactive functional group is a carboxyl group.

5. The method according to claim 1, wherein the saccharide is a polysaccharide.

6. The method according to claim 1, wherein the saccharide includes a saccharide having a carboxyl group.

7. The method according to claim 1, wherein the saccharide includes carboxymethyl cellulose.

8. The method according to claim 1, wherein the saccharide is chemically bound to the base material.

9. The method according to claim 1, wherein the binding of the solid-phase carrier to the lipophilic ligand is carried out in a solvent having a water content of less than 50% by mass.

10. A solid-phase carrier for capturing a target substance, comprising a base material which is a particle having a particle diameter of from 0.5 to 10 μm, at least a portion of the surface thereof being formed of or coated with a saccharide, and a linker comprising a polyalkylene glycol chain in a structure thereof and having a reactive functional group for binding a lipophilic ligand that specifically binds to the target substance and that has a Log P value of 0 or more, the Log P value being a log value of an octanol/water partition coefficient, wherein the number of atoms of the linker is 20-100, provided that the number of atoms of the linker is the number of atoms when the lipophilic ligand is bound to the linker and is the number of atoms counted from a starting point at the atom adjacent to the saccharide ring structure to an end point at the reactive functional group to be used for the binding of the lipophilic ligand, and that when the linker has a ring structure or the linker has a branched chain structure and has plural starting points and/or end points, the number of atoms of the linker is the minimum number of atoms from the starting point to the end point, and the saccharide is chemically bound to the linker.

11. The solid-phase carrier according to claim 10, wherein the content of the reactive functional group is 1 to 400 μmol/g.

12. The solid-phase carrier according to claim 10, wherein the content of the reactive functional group is 0.1 to 100 square Å/reactive functional group in terms of a parking area.

13. A method for producing a ligand bound solid-phase carrier for capturing a target substance, comprising binding the solid-phase carrier according to claim 10 to a lipophilic ligand.

14. A ligand bound solid-phase carrier for capturing a target substance, produced by the production method according to claim 13.

15. The method according to claim 9, wherein the solvent comprises at least one selected from the group consisting of an amide and a sulfoxide.

16. The method according to claim 9, wherein the solvent comprises at least one selected from the group consisting of N,N-dimethylformamide, hexamethylphosphoric triamide, N-methylpyrrolidone, 1,3-dimethyl-2-imidazoline, and dimethyl sulfoxide.

* * * * *